(12) United States Patent
Schall et al.

(10) Patent No.: US 11,207,121 B2
(45) Date of Patent: Dec. 28, 2021

(54) COAGULATION DEVICE COMPRISING AN ENERGY CONTROL

(71) Applicant: Erbe Elektromedizin GmbH, Tuebingen (DE)

(72) Inventors: Heiko Schall, Nuertingen (DE); Daniel Schaeller, Tuebingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 832 days.

(21) Appl. No.: 15/971,804

(22) Filed: May 4, 2018

(65) Prior Publication Data

US 2018/0250063 A1 Sep. 6, 2018

Related U.S. Application Data

(63) Continuation of application No. 14/285,189, filed on May 22, 2014, now Pat. No. 9,962,218.

(30) Foreign Application Priority Data

May 24, 2013 (EP) .................................... 13169105

(51) Int. Cl.
*A61B 18/12* (2006.01)
*A61B 18/00* (2006.01)

(52) U.S. Cl.
CPC .. *A61B 18/1206* (2013.01); *A61B 2018/0063* (2013.01); *A61B 2018/00589* (2013.01);
(Continued)

(58) Field of Classification Search
CPC ...... A61B 18/1206; A61B 2018/00589; A61B 2018/00619; A61B 2018/0063;
(Continued)

(56) References Cited

U.S. PATENT DOCUMENTS 5,330,471 A 7/1994 Eggers
6,733,498 B2 5/2004 Paton et al.
(Continued)

FOREIGN PATENT DOCUMENTS

EP 0717967 A2 6/1996
EP 1862137 A1 12/2007
(Continued)

OTHER PUBLICATIONS

European Search Report in European Application No. 13169105.7 dated Sep. 10, 2013, 6 pages.
(Continued)

*Primary Examiner* — Khadijeh A Vahdat
(74) *Attorney, Agent, or Firm* — Fitch, Even, Tabin & Flannery LLP

(57) ABSTRACT

A device (10) for tissue coagulation, in particular for fusion, encompasses an electric source (18), which is connected or which can be connected to electrodes (12, 13) for influencing biological tissue (11) with current. A control unit (22) controls the source (18) during phases I and II of the tissue fusion. These phases I and II correspond to operating phases I, II and III of the device (10). During operating phase I, a monitoring unit (23) determines the energy $E_1$, which is applied into the tissue (11). In the subsequent operating phases II and III, the control unit (22) controls the source (18) by means of the determined energy $E_1$. Such a device turns out to be particularly reliable and to be robust in use.

15 Claims, 2 Drawing Sheets

(52) U.S. Cl.
CPC ............ *A61B 2018/00619* (2013.01); *A61B 2018/00666* (2013.01); *A61B 2018/00702* (2013.01); *A61B 2018/00761* (2013.01); *A61B 2018/00779* (2013.01); *A61B 2018/00827* (2013.01); *A61B 2018/00892* (2013.01)

(58) Field of Classification Search
CPC ........... A61B 2018/00666; A61B 2018/00702; A61B 2018/00761; A61B 2018/00779; A61B 2018/00827; A61B 2018/00892
USPC ...................................................... 606/41–50
See application file for complete search history.

(56) References Cited

U.S. PATENT DOCUMENTS

| | | |
|---|---|---|
| 8,034,049 B2 | 10/2011 | Odom et al. |
| 8,147,485 B2 | 4/2012 | Wham et al. |
| 8,216,223 B2 | 7/2012 | Wham et al. |
| 2010/0179563 A1 | 7/2010 | Skakoon et al. |
| 2011/0160725 A1 | 6/2011 | Kabaya et al. |
| 2013/0006237 A1 | 1/2013 | Werner |

FOREIGN PATENT DOCUMENTS

| | | |
|---|---|---|
| EP | 2213255 A1 | 8/2010 |
| EP | 2394593 A1 | 12/2011 |
| EP | 2499982 A1 | 9/2012 |
| JP | H07500514 A | 1/1995 |
| JP | 2012192188 A | 10/2012 |
| JP | 2013013720 A | 1/2013 |
| WO | 2008102154 A2 | 8/2008 |

OTHER PUBLICATIONS

Office action in Korean application No. 10-2014-0061504, dated Aug. 19, 2015, 7 pages.
Office action in Korean application No. 10-2014-0061504, dated Feb. 24, 2016, 4 pages.
Office action in Japanese application No. 2014-107828, dated Jun. 2, 2015, 13 pages.
Search report in Japanese application No. 2014-107828, dated May 31, 2015, 66 pages.
Office action in Japanese application No. 2014-107828, dated Oct. 13, 2015, 5 pages.

COAGULATION DEVICE COMPRISING AN ENERGY CONTROL

RELATED APPLICATION(S)

This application is a continuation of U.S. patent application Ser. No. 14/285,189 filed May 22, 2014, now U.S. Pat. No. 9,962,218, which claims the benefit of European Patent Application No. 13169105.7 filed May 24, 2013, the contents of each application being incorporated herein by reference as if fully rewritten herein.

TECHNICAL FIELD

The invention relates to a device for tissue coagulation, in particular for tissue fusion.

BACKGROUND

Various electrosurgical methods, the effect of which is based on a controlled denaturation of biological tissue, are in use.

For example, EP 1 862 137 A1 discloses a coagulation device comprising a generator, which feeds two electrodes, between which biological tissue is seized. During the coagulation, the tissue runs through a first phase I, during which the tissue impedance decreases considerably, and a second phase II, during which the tissue impedance increases again. To determine the tissue impedance, provision is made for a sensor circuit, which transmits a query signal, so as to determine the initial tissue impedance and so as to subsequently define a certain trajectory for the desired course of time of the tissue impedance. The query signal is formed by means of an electric pulse, by means of which a tissue characteristic is measured. The measured tissue characteristic can be energy, power, impedance, current, voltage, electric phase angle, reflected power or temperature.

U.S. Pat. No. 8,216,223 B2 also deals with the coagulation of tissue. The tissue impedance is initially measured during an HF activation of electrodes. Over the course of time, the minimum of the impedance is established. Starting at this point, a reference value curve is generated for the desired impedance increase and a target value is calculated for the impedance. Once the latter has been reached, the HF generator is turned off. The turn-off is followed by a cooling phase, the length of which is also provided by the reference value curve. The fusion is concluded with the end of the cooling phase.

The thermofusion according to U.S. Pat. No. 8,034,049 B2 is also controlled by means of the initial tissue impedance. In phase I of the thermofusion, the course of the impedance is measured in response to current, which is kept constant, for example. The initial impedance, the decrease of the impedance, the minimum of the impedance or the increase of the impedance are derived from this. Other activation parameters are generated from this information.

EP 2 213 255 B1 describes the control of the energy in response to a thermofusion. A state variable SV, which indicates the decrease or increase of the impedance, is generated for this purpose. A reference value trajectory is provided for the impedance. The energy input is controlled such that the desired chronological course of the impedance is approximated. For this purpose, the energy input is coupled or countercoupled as a function of the state variables SV to the impedance.

EP 2 394 593 A1 describes the measuring of the impedance during the thermofusion. Provision is made to check, whether, after a certain minimum time has lapsed, a minimum impedance has been reached. As soon as this is the case, the activation is concluded.

U.S. Pat. No. 6,733,498 B2 discloses a method for thermofusion, in the case of which the chronological course of the tissue impedance is determined during the application of HF voltage. The end of the first phase and the duration of the second phase are defined accordingly by means of the course of the impedance.

U.S. Pat. No. 8,147,485 B2 also uses the monitoring of the tissue impedance for regulating the thermofusion. An impedance trajectory is calculated from the minimum of the tissue impedance and the impedance increase.

U.S. 2010/0179563 A1 and U.S. 2011/0160725 A1 also determine the tissue impedance or the change thereof for controlling or regulating the electrosurgical process.

The local state of tissue is characterized by the local specific tissue impedance. Even though the determination of the impedance between two electrodes provides an indication for the state and thus for the treatment progress of the tissue as a whole, the local specific tissue impedance, however, is not determined. This can lead to incorrect conclusions in the case of inhomogeneous tissue.

SUMMARY

It is the task of the invention to create an alternative device for tissue coagulation.

The device according to the invention serves the purpose of tissue coagulation and, if necessary, also tissue fusion. For this purpose, an electric source is connected or can be connected to electrodes for influencing biological tissue with current. The electric source can be a source for direct current or alternating current, preferably HF current. Preferably, the source is embodied in a controllable manner, so as to be able to control the size of the output current and/or of the output voltage. For this purpose, said source is connected to a control unit. The latter includes a monitoring unit, which is connected to the source. In particular, the monitoring unit is connected to the output of the source, to which the electrodes are connected as well. In the alternative, the monitoring unit can be connected to the electrodes. The monitoring unit thus determines at least an electric variable, which characterizes the energy, which was output from the source to the electrodes and thus from the electrodes to the tissue during a first operating phase. The first operating phase corresponds to phase I of the tissue coagulation, during which the tissue resistance decreases and passes through a minimum.

For example, the monitoring unit can determine the current power and can integrate it during the first operating phase, so as to establish the output energy. It is advantageous in particular, if the monitoring unit determines the active power, which is output by the electrodes. By means of integration, the active energy, which was converted thermally in the tissue, is established from this. The energy, which was input into the tissue in the first operating phase, is used to control the second operating phase. The latter corresponds to phase II of the tissue coagulation, during which the tissue resistance increases and the tissue dries by boiling tissue fluid.

In the alternative, the apparent power, which, however, includes idle power portions, can be determined. If said idle power portions are known or constant, the apparent power and thus the total apparent energy, which was output, can also be used to control the second operating phase.

The control unit controls the source in the second operating phase by means of the energy (active energy or apparent energy), which was established during the first operating phase. It is ensured through this that the energy quantity applied in the second operating phase is adapted to the size of the tissue area, which is determined and influenced by the electrodes. The cells, which are open in the first phase I, release tissue fluid. In the second phase II, said tissue fluid is evaporated by drying the tissue. By determining the energy, which was applied in the first operating phase, a parameter is available, by means of which phase II can be controlled such that the entire tissue, which was influenced electrosurgically in phase I, is coagulated evenly.

It is advantageous, if the control unit operates the source in the first operating phase I by means of a regulated current. At the onset, it is thereby possible to provide a chronologically increasing current as well as a constant current in the further course of the operating phase I. This results in a heat-up of the tissue and in a heat-up of the electrodes. Thermal tissue denaturation results in a decrease of the tissue impedance, which can be between 2 Ohm and 40 Ohm, for example. Due to vapor formation and beginning drying of the tissue, the impedance can increase again during operating phase I, until the end of phase I is recognized. Various recognition criteria can be used for this purpose. For example, the relationship between voltage and current at the source and thus the tissue impedance can increase beyond a threshold value. In the alternative, it can be used as recognition criterion, if the relationship between voltage and current at the source, that is, the tissue impedance, passes through a minimum. As a further alternative, it can be used as recognition criterion that the voltage at the source exceeds a threshold value. As a further alternative, it can be used as recognition criterion that the current, which is to be kept constant by the source, falls below a threshold value, because the current regulating circuit formed by the control unit and the source leaves its control range. This can take place, when the source has reached its maximum voltage or another voltage limit. In the alternative, the speed of the change of the tissue resistance (relationship between voltage and current at the source) can also be used as turn-off criterion, for example in that a limit is determined for the increase speed of the tissue impedance and the reaching thereof is monitored.

In any event, the energy applied so far is stored at the end of the operating phase I. The progress of further controlling operating phase II is derived from this energy value. In particular, the duration of operating phase II can be defined according to the energy value from operating phase I. The turn-off criterion, that is, the end of a subsequent operating phase III, can also be defined by means of the energy value determined in the first operating phase. The control parameters, that is, the duration of operating phase II and the turn-off criterion, that is, the end of operating phase III, are thus functions of the energy measured in operating phase I. Preferably, the transition from operating phase I to operating phase II takes place continuously, that is, without abrupt change of the current supplied to the biological tissue and/or without abrupt change of the voltage applied to the tissue and/or without abrupt change of the power output to the tissue.

In operating phase II, the control unit preferably operates the source in an impedance-controlled manner as reference value of the impedance increase. A value of above 100 Ohm per second is recommended for the tissue impedance. The specific slow increase of the impedance causes a stabilization of the evaporation of tissue fluid. The vapor formation takes place evenly and in a spatially distributed manner. The desired chronological course of the impedance can have a constant increase or also a variable increase. Preferably, the control unit defines the chronological length of operating phase II as a function of the energy determined in the first operating phase. The second operating phase is concluded, when the time $t_2$ has elapsed. The third operating phase III follows (optionally). During the latter, a constant voltage is preferably applied to the biological tissue.

The end of the third operating phase III can be defined in that the minimum treatment time has elapsed and an energy $E_{tot}$ has been reached. The energy $E_{tot}$ can be defined as a function of the energy $E_1$ determined in the first operating phase. The minimum treatment time $t_{min}$ can also be determined by the energy $E_1$. In the alternative, the operating phase III can be concluded, when the maximum treatment time has elapsed. The latter, in turn, can be defined as a function of the minimum treatment time and thus also as a function of the energy $E_1$ determined in the first operating phase. Further turn-off criteria, which in each case are a function of the energy $E_1$, can be defined.

During the course of the treatment, it may happen that treatment parameters change. For example, inadvertent temporary loosening of the electrodes from the biological tissue (opening of fusion clamps), seeping tissue fluid, such as blood or rinsing fluid, can influence the process. It may thus become necessary that a larger quantity of energy and longer application time becomes necessary, than was originally derived from the energy $E_1$. To attain proper fusion in such cases, the current power can be monitored during the second (and/or third) operating phase. Provided that the power within a monitoring time interval leaves a predetermined window of minimum power $P_{min}$ and maximum power $P_{max}$ for a non-negligibly short period of time, the application time, that is the times $t_2$ and $t_3$, as well as calculating parameters $t_{min}$ and/or $t_{max}$ can be lengthened accordingly.

Further details of embodiments of the invention follow, from the drawing and/or from the following description of an illustrative example:

DETAILED DESCRIPTION

Figure 1:
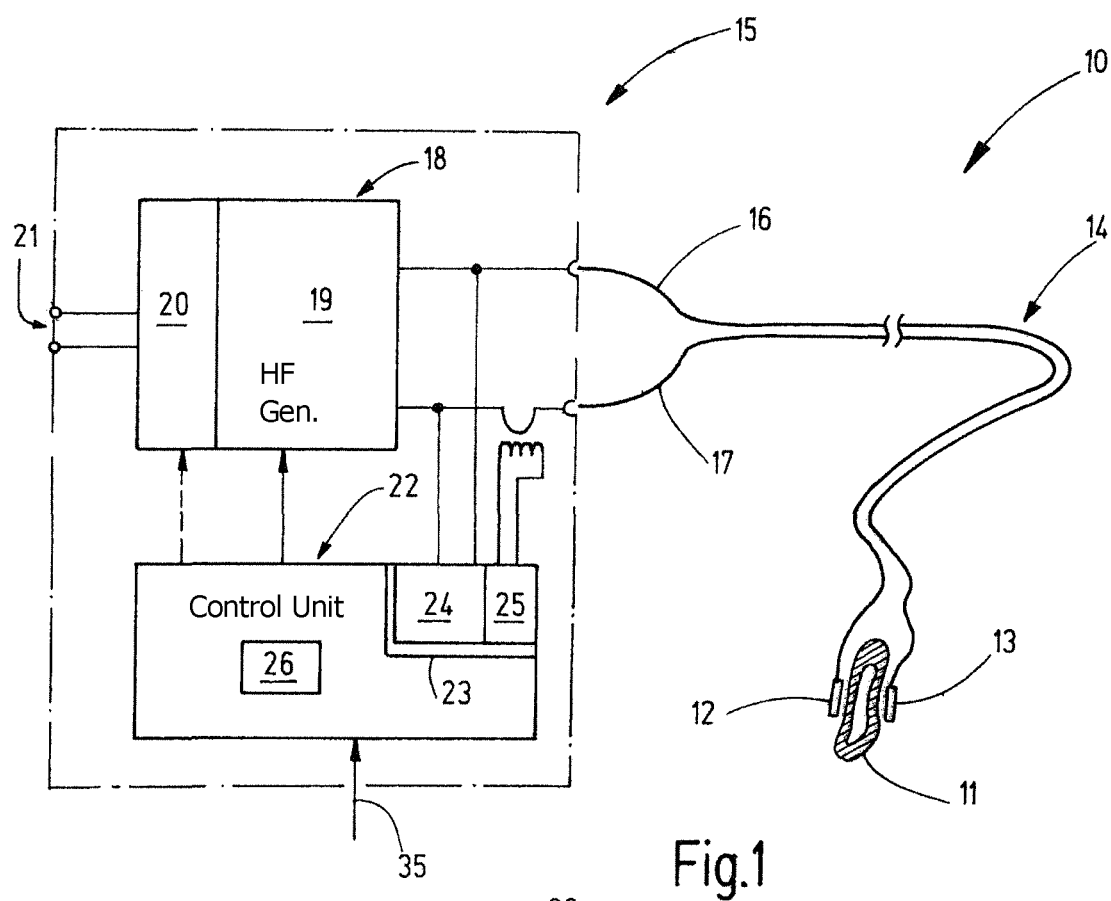
FIG. 1 shows the device according to the invention in schematic illustration.

FIG. 1 illustrates a device 10 for coagulating biological tissue 11, which can be a hollow vessel or also any other biological tissue, for example. In the following example, a blood vessel is illustrated as tissue 11, which is to be closed by means of coagulation, that is, a fusion of the walls of the vessel, which are located opposite one another, is to be carried out. Two electrodes 12, 13, which can seize the tissue 11 between one another and which can also stress it mechanically, for example by means of compression, serve this purpose. The mechanical structure of the corresponding instrument is not illustrated in detail in FIG. 1. For example, the electrodes 12, 13 can be the branches of a bipolar fusion instrument.

The electrodes 12, 13 are connected to a feeding device 15 via a line 14. For this purpose, the line 14 encompasses two leads 16, 17, for example, to which the device 15 supplies or can supply high-frequency current.

For this purpose, the device 15 encompasses a source 18, for example in the form of a controllable HF generator 19. The latter can be supplied with operating voltage via a power supply 20 and a power connector 21 via a mains power supply.

The HF generator 19 and/or the power supply 20 are embodied so as to be controllable. At their corresponding controls inputs, a control unit 22, which controls or regulates in particular the output of electric power through the HF generator 19, is connected, as is illustrated by means of arrows. For this purpose, the control unit 22 includes a monitoring unit 23, which determines the electric variables of the electric energy, which is supplied to the electrodes 12, 13. In particular, the monitoring unit 23 is equipped to determine and integrate the electric power supplied to the electrodes 12, 13 at least temporarily, so as to establish the energy, which is supplied during a time interval. The monitoring unit 23 can encompass a voltage block 24 for monitoring the voltage applied at the clamps 12, 13. In addition, the monitoring unit 23 can encompass a current block 25 for establishing the size of the current, which is supplied to the electrodes 12, 13. The control unit 22 can furthermore encompass a module 26 for defining the conclusion of a first operating phase I, wherein the module receives at least one output signal from the voltage block 24 or from the current block 25 or a signal derived from the output signals thereof for recognizing the end of the operating phase.

Figure 2:
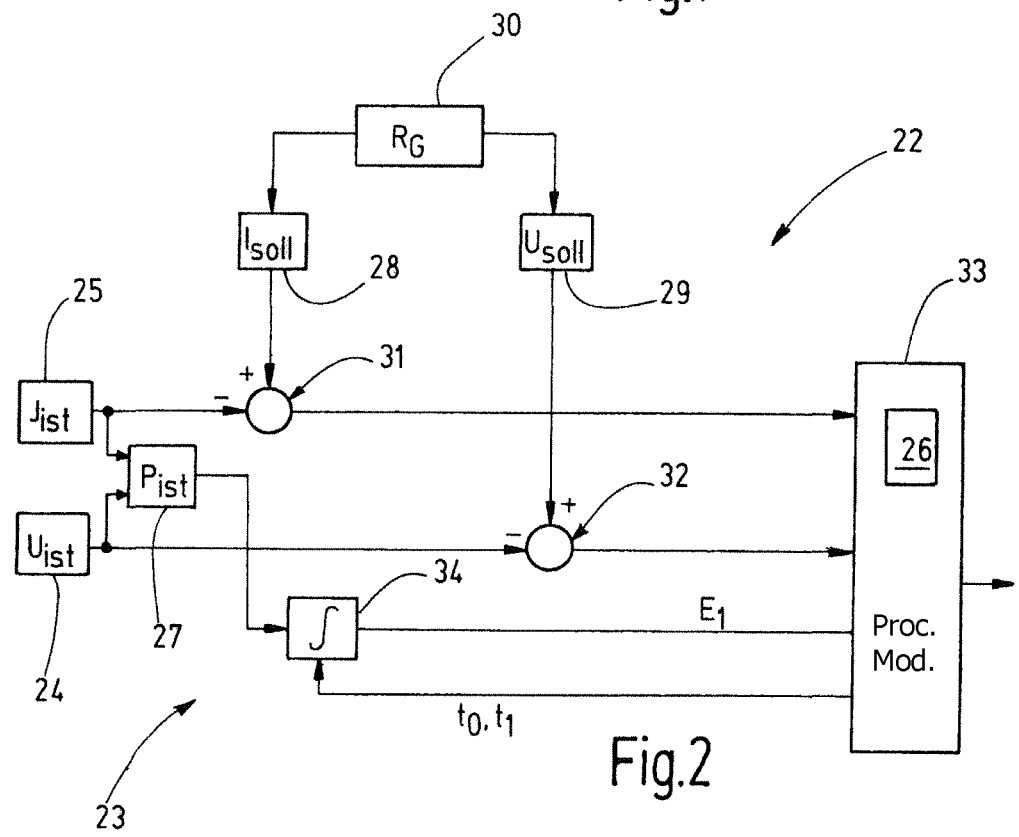
FIG. 2 shows a control unit for the device according to FIG. 1, in a sectional schematized block diagram

In FIG. 2, the control unit 22 is illustrated in a schematically simplified manner and only in excerpts. The current block 25 determines the current $I_{ACT}$, which flows through the tissue 11. The actual voltage $U_{ACT}$, which is applied to the tissue 11, is determined by means of the voltage block 24. The power $P_{ACT}$, which is actually supplied to the tissue 11, is calculated from both variables, at least temporarily. The power $P_{ACT}$ can be the determined active power or also the apparent power, which is supplied to the electrodes 12, 13. A corresponding block serves the purpose of calculating the power $P_{ACT}$ or for determining it otherwise.

The control unit 22 can furthermore encompass a current default block 28, which provides a current $I_{REF}$ as a function of time and/or situation. Likewise, provision can be made for a voltage default block 29, so as to provide a desired voltage $U_{REF}$. The current default block 28 and the voltage default block 29 can be controlled by an impedance block 30, which defines a desired relationship between the voltage $U_{REF}$ and the current $I_{REF}$ as a function of time or situation, for example so as to define a desired tissue resistance $R_G$ or a desired chronological course thereof.

The reference-actual deviations for the current $I_{ACT}$ and the voltage $U_{ACT}$ are in each case formed in corresponding differential forming blocks 31, 32 and are supplied to a processing module 33. The latter controls the generator 19.

The processing module 33 furthermore includes the module 26 for recognizing various operating phases. This module 26 can obtain at least the actual current $I_{ACT}$ and/or the actual voltage $U_{ACT}$ or a value, which is derived from these variables, as input variable (via non-illustrated signal paths).

An energy block 34 for determining the energy supplied to the tissue 11 is connected to the block 27 for establishing the power. Said energy block integrates the measured power $P_{ACT}$ for a period of time, which is provided by the processing module 33, and supplies the integral to the processing block 33.

It is pointed out that the blocks 27 to 32 as well as 34 can also be part of the processing module 33.

The further design of the device 15 and in particular of its control unit 22 follows from the following description of the time behavior thereof:

It is assumed that living, non-denaturized tissue 11, is initially seized between the electrodes 12, 13. At its activation input 35, the device 15 now receives the signal for coagulation and, if applicable, for fusion of the biological tissue 11. This corresponds to the starting point or activation onset $t_0$, respectively, which is noted in FIG. 3. Operating phase I initially starts with a partial phase Ia. In the latter, the current $I_{ACT}$ is brought to a desired current value of 4 A, for example, in a controlled manner. The current can thereby be brought from an initial value, such as 1 A, for example, to the reference value of 4 A, for example, within a period of time $t_{1a}$. This can take place in a linear ramp: the time for this can be between 200 ms and 2 s. Preferably, the effective value of the current is used as measuring variable. The tissue resistance $R_G$ decreases from an initial value to a minimum value of between 2 Ohm and 40 Ohm, for example, during this phase or also completely or partially in a later operating phase Ib. Due to the increase of the current, the voltage $U_{ACT}$ increases during the time period $t_{1a}$. During this time, the current $I_{ACT}$ is preferably increased in the form of a ramp. For example, the peak voltage between the electrodes 12, 13 can be measured as measuring value for the voltage $U_{ACT}$. In operating phase I, the current $I_{ACT}$ is then held constant at the value $i_{1b}$ during a further partial phase Ib. The control unit 22 thereby operates as current regulating circuit for keeping the value $i_{1b}$ constant.

During the first partial phase Ia or during the second partial phase Ib, the tissue resistance $R_G$ passes through a minimum, so as to then increase again. If the tissue resistance minimum is already reached in the first partial phase Ia, the partial phase Ib can be skipped and a direct transition into operating phase II can be made. The power limit of the generator 19 might possibly be reached thereby, so that the current regulating circuit is no longer able to bring the current $I_{ACT}$ into conformity with the desired current $I_{REF}$. Towards the end of operating phase I, the current thus decreases. Depending on the embodiment, this decrease of the current $i_{1b}$ or also the current differential value ($I_{REF}-I_{ACT}$), which is formed by the differential forming block 31, can be used as indicator for the conclusion of operating phase I. It is also possible for the control unit 22 to establish the tissue impedance $R_G$ as quotient from $U_{ACT}$ and $I_{ACT}$ and to determine the conclusion of operating phase I, if the tissue resistance exceeds a given threshold. In the alternative, the increase speed for the tissue resistance $R_G$ can also be monitored. According to this, the control unit 22 can use the following criteria to recognize operating phase I, either cumulatively or as alternatives:

- detecting the pass-through of the minimum of the tissue impedance or of the tissue resistance dR/dt=0)
- falling below a threshold value of the current $I_{ACT}$, for example $0.5*i_{1b}$
- exceeding a threshold value of the tissue impedance, for example 80 Ohm
- exceeding a threshold value of the increase speed of the tissue impedance (dR/dt).

During the entire operating phase I, the energy block 34 integrates the power established by the block 27 and supplies the established value of the energy $E_1$ to the processing module 33 at the conclusion of operating phase I. The onset and the conclusion of operating phase I are marked by means of the points in time $t_0$ and $t_1$. The point in time $t_1$ is determined by the processing module 33 according to one of the above-mentioned criteria.

Figure 3:
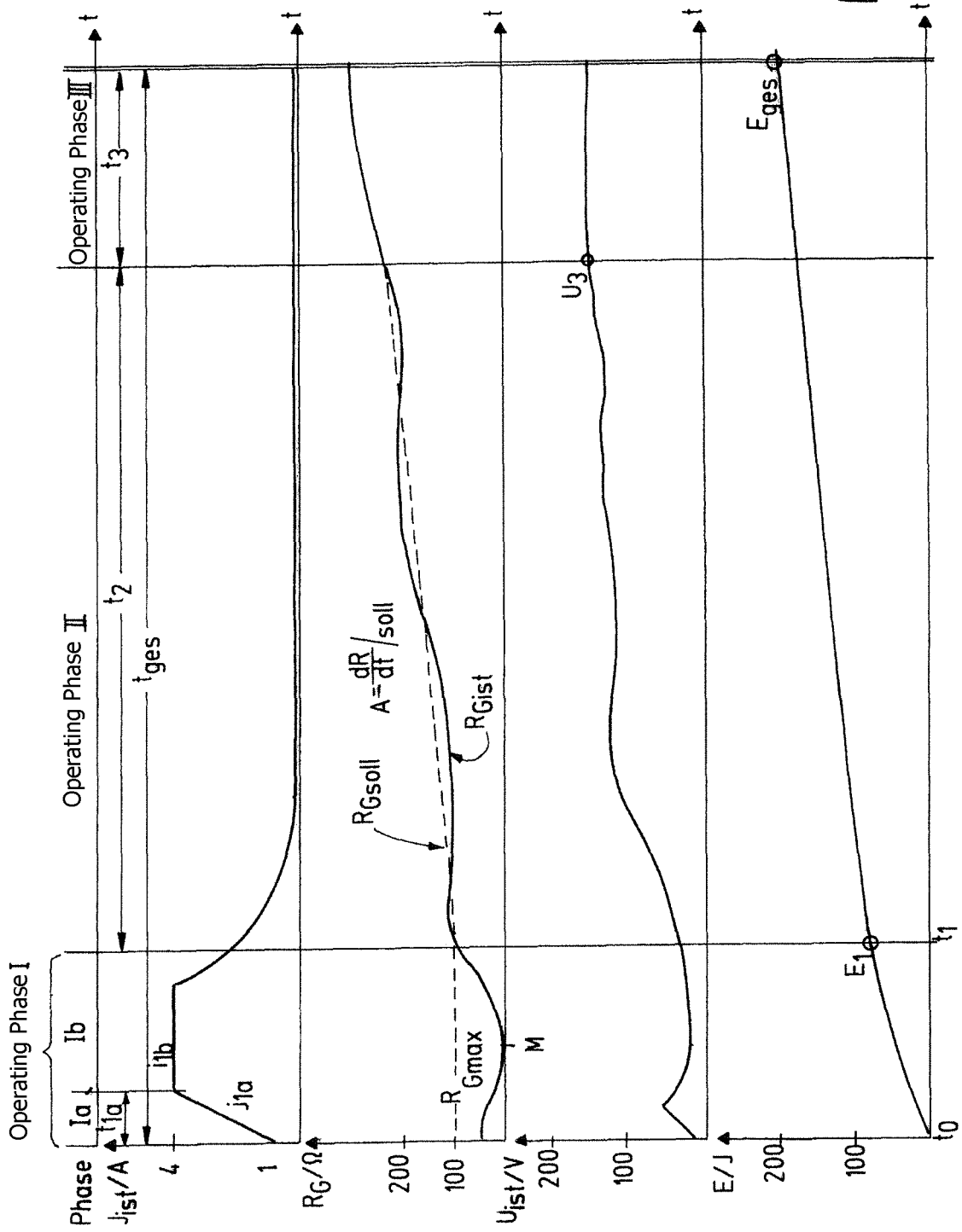
FIG. 3 shows time diagrams for explaining the function of the control unit.

Operating phase II starts with the conclusion of operating phase I. Operating phase II preferably starts with the same current $I_{ACT}$, with which operating phase I concluded. In addition, it preferably begins with the same voltage $U_{ACT}$, with which the first operating phase I concluded. Operating criteria are now defined for operating phase II by means of the applied energy $E_1$, which was established in operating phase I. In operating phase II, the generator 19 is preferably operated in an impedance-regulated manner, that is, the control unit 22 forms a regulator for the tissue impedance. A desired chronological impedance increase A is defined for the tissue impedance. In FIG. 3, the impedance increase A is illustrated as $R_{Gref}$ as desired dashed line over the course of time. The actual impedance increase $R_{Gact}$ can deviate slightly from this. This depends on the control quality of the impedance regulator, which is now formed by the control unit 22. At the same time, the current $I_{ACT}$ decreases during operating phase II, that is, during the period of time $t_2$, while the voltage $U_{ACT}$ increases. The voltage $U_{act}$ has an upper limit, e.g. 150V (peak value), so that it is avoided that sparks appear and that a cutting effect would thus be caused.

The impedance increase A can be between 50 and 200, preferably 100 Ohm per second. The specific slow increase of the impedance causes a stabilization of the evaporation of the tissue fluid.

Operating phase II is concluded, when the period $t_2$ has elapsed. The period $t_2$ can be established from the energy $E_1$ as follows:

$$t_2 = 2/3(t_{max} - t_1).$$

The time $t_{max}$ is thereby the maximum treatment period. The maximum treatment period $t_{max}$ can be calculated from the minimum treatment period, in that a constant defined summand is added, for example:

$$t_{max} = t_{min} + 1.8 \text{ s}$$

The minimum treatment period $t_{min}$ can be determined, for example, from the following relationship from the energy $E_1$:

$$t_{min} = \min\{5.4 \text{ s}; (-38.25 \text{ } \mu s * E_1^2/J^2 + 18 \text{ ms} * E_1/J + 270 \text{ ms})\}.$$

According to this, $t_{min}$ is a defined value of 5.4 s, for example, or which results from calculating the round bracket, depending on which value is less.

With the conclusion of operating phase II, operating phase III begins. In the latter, the voltage $U_{ACT}$ is constantly regulated to the value $U_3$ for a period of time $t_3$. The control unit 22 operates as a voltage regulator circuit herein.

During operating phases II and III, which correspond to phase II of the tissue coagulation, the power is integrated further. When this value reaches the total maximum value $E_{tot}$, the treatment is concluded. The total maximum value $E_{tot}$ can be established according to various empirically obtained formulas as a function of the energy $E_1$, for example as follows:

$$E_{tot} = 45J + 2.75 * E_1.$$

In the alternative, the reaching of the maximum period $t_3$ of operating phase III can be recognized. This period $t_3$ can be calculated, for example according to:

$$t_3 = 1/3 * (t_{max} - t_1).$$

To avoid improper treatments caused by unforeseen changes of the treatment parameters, for example by accidentally opening the fusion clamps, it can additionally be monitored, whether the actual power leaves a performance window from $P_{min}$ and $P_{max}$ within a monitoring time interval, for example during operating phase II and/or III.

A device 10 for tissue coagulation, in particular fusion, encompasses an electric source 18, which is connected or can be connected to electrodes 12, 13 for influencing biological tissue 11 with current. A control unit 22 controls the source 18 during phases I and II of the tissue fusion. These phases I and II correspond to operating phases I, II and III of the device 10. During operating phase I, a monitoring device 23 determines the energy $E_1$, which is applied into the tissue 11. The control unit 22 controls the source 18 in the subsequent operating phases II and III by means of the determined energy $E_1$. Such a device turns out to be particularly reliable and to be robust in use.

LIST OF REFERENCE NUMERALS 10 device
11 biological tissue
12, 13 electrodes
14 line
15 device
16, 17 leads
18 source
19 HF generator
20 power supply
21 power connector
22 control unit
23 monitoring unit
24 voltage block
25 current block
26 module for recognizing operating phases
$U_{ACT}$ voltage (e.g. peak value)
$I_{ACT}$ current (e.g. effective value)
$P_{ACT}$ power
27 block for establishing power
28 current default block
$I_{ACT}$ desired current
29 voltage default block
$U_{REF}$ desired voltage
30 impedance block
$R_G$ tissue resistance
31, 32 differential forming blocks
33 processing module
34 energy block
35 activation input
$t_0$ activation onset
I first operating phase
Ia partial phase
$t_{1a}$ period of the first partial phase
Ib partial phase
$i_{1a}$ value of the current $I_{ACT}$ in the partial phase Ia
$i_{1b}$ value of the current $I_{ACT}$ in the partial phase Ib
$t_1$ period of operating phase I
$E_1$ energy input into the tissue 11 in phase I
A impedance increase
$R_{Gref}$ desired impedance course
$R_{Gact}$ actual impedance course
$t_2$ period of operating phase II
$t_{max}$ maximum period of treatment
$t_{min}$ minimum period of treatment
$E_{tot}$ total maximum value of the energy
$t_3$ period of operating phase III
$t_{tot}$ total period of treatment $R_{Gmax}$ threshold value for tissue resistance in operating phase I
M minimum of the tissue resistance in operating phase I
$U_3$ voltage in operating phase III
$P_{max}$, $P_{min}$ define performance windows for the power P of the source 18 in operating phases II and/or III

What is claimed is:

1. A device (10) for tissue coagulation, the device comprising:
   an electric source (18), configured to be connected to electrodes (12, 13) for influencing biological tissue (11) with current,
   a monitoring unit (23), which is connected to the electric source (18), configured to determine one or both of a current ($I_{ACT}$) output by the electric source (18) and a voltage ($U_{ACT}$) output by the electric source (18),
   a control unit (22), which includes the monitoring unit (23) and which is connected to the electric source (18) in a controlling manner, the control unit (22) configured to:
      determine an energy value (E1) which corresponds to a total amount of energy the electric source (18) outputs to the electrodes (12, 13) during a first operating phase (I), and
      control the electric source (18) as a function of the energy value (E1), which is determined in the first operating phase (I), in a subsequent second operating phase (II), wherein at least one of a minimum and a maximum duration of the second operating phase (II) is defined according to the energy value (E1) from the first operating phase (I).

2. The device according to claim 1, wherein the control unit (22) is interconnected with the electric source (18) in the first operating phase (I) as a current regulating circuit.

3. The device according to claim 1 wherein at an onset of the first operating phase (I), the control unit (22) is configured to define a chronologically increasing current (i1a).

4. The device according to claim 1 wherein during at least a section (Ib) of the first operating phase (I), the control unit (22) is configured to define a constant current (i1b).

5. The device according to claim 1 wherein the control unit (22) comprises a module (26) configured to determine a conclusion of the first operating phase (I) using at least one of:
   a relationship between voltage and current at the electric source (18) increases beyond a threshold value ($R_{Gmax}$),
   the relationship between voltage and current at the electric source (18) passes through a minimum (M),
   an increased speed of change in the relationship between voltage and current at the electric source (18) exceeds a threshold value,
   the voltage ($U_{ACT}$) at the electric source (18) exceeds a threshold value,
   the current ($I_{ACT}$) falls below a threshold value.

6. The device according to claim 1 wherein at an onset of the second operating phase (II), the control unit (22) is equipped to adjust at least one variable of:
   current ($I_{ACT}$) from the electric source (18),
   voltage ($U_{ACT}$) at the electric source (18),
   output power ($P_{ACT}$) of the electric source (18) to a same value the variable had at a conclusion of the first operating phase (I).

7. The device according to claim 1 wherein in the second operating phase (II), the control unit (22) is configured to define a course of time for changing of a relationship between the voltage ($U_{ACT}$) at the electric source (18) and the current ($I_{ACT}$) supplied by said source.

8. The device according to claim 7, wherein the course of time encompasses a constant impedance increase (A).

9. The device according to claim 1 wherein the control unit (22) is configured to define a chronological length (t2) of the second operating phase (II).

10. The device according to claim 1 wherein the control unit (22) is configured to define a chronological length (t2) of the second operating phase (II) as a function of the energy value (E1), which is determined in the first operating phase (I).

11. The device according to claim 1 wherein directly following the second operating phase (II), the control unit (22) is configured to merge into a third operating phase (III).

12. The device according to claim 11, wherein in the third operating phase (III), the control unit (22) is configured to define and adjust a constant voltage (U3).

13. The device according to claim 11, wherein in the third operating phase (III), the control unit (22) is configured to define a voltage (U3) of the electric source (18) to a value determined by the monitoring unit (23) at a conclusion of the second operating phase (II).

14. The device according to claim 11, wherein the control unit (22) is configured to conclude the third operating phase (III), if:
   a minimum treatment time ($t_{min}$) and a given total energy ($E_{tot}$) have been reached or
   a maximum treatment time ($t_{max}$) has elapsed or
   a maximum energy ($E_{max}$) has been applied.

15. The device according to claim 11, wherein the control unit (22) is equipped to monitor a power output by the electric source (18) in the operating phase (II), so as to extend a time period (t2) for the second or third operating phase (II, III), provided that the power has left a performance window, which is defined between a maximum power ($P_{max}$) and a minimum power ($P_{min}$).

* * * * *